United States Patent
Basoglu et al.

(10) Patent No.: US 8,197,540 B2
(45) Date of Patent: Jun. 12, 2012

(54) OCULAR IMPLANT IRIS DIAPHRAGM

(75) Inventors: Ayhan Basoglu, Pittsfield, MA (US);
Richard Albert Vaneagas, New York, NY (US)

(73) Assignee: Stellar Devices LLC, New York, NY (US)

(*) Notice: Subject to any disclaimer, the term of this patent is extended or adjusted under 35 U.S.C. 154(b) by 184 days.

(21) Appl. No.: 12/767,527

(22) Filed: Apr. 26, 2010

(65) Prior Publication Data

US 2011/0264212 A1    Oct. 27, 2011

(51) Int. Cl.
*A61F 2/14* (2006.01)
(52) U.S. Cl. ......................................................... 623/4.1
(58) Field of Classification Search .............. 623/6.36, 623/4.1, 6.14, 6.38–6.41, 6.43–6.47, 6.49
See application file for complete search history.

(56) References Cited

U.S. PATENT DOCUMENTS

| | | |
|---|---|---|
| 6,079,417 A | 6/2000 | Fugo |
| 6,280,469 B1 | 8/2001 | Terry et al. |
| 7,025,781 B2 | 4/2006 | Kahn |
| 2004/0153148 A1* | 8/2004 | Kahn ............................ 623/4.1 |
| 2005/0015143 A1* | 1/2005 | Willis et al. ................. 623/6.36 |
| 2006/0253196 A1* | 11/2006 | Woods ......................... 623/6.13 |
| 2006/0271184 A1* | 11/2006 | Silvestrini ................... 623/5.16 |
| 2007/0088432 A1 | 4/2007 | Solovay et al. |

* cited by examiner

*Primary Examiner* — David H Willse
*Assistant Examiner* — Tiffany Shipmon
(74) *Attorney, Agent, or Firm* — Louis Ventre, Jr.

(57) ABSTRACT

An ocular implant alters iris color for medical and cosmetic purposes and is made of an inert, nontoxic, foldable and preferably permeable to fluid flow material. It is an annular non-planar structure that fits over the iris yet leaves the natural lens uncovered and extends approximately to the iridocorneal angle. Two different kinds of arc sections of a non-uniform thickness make up the structure: passage arc sections and support arc sections. The passage arc sections permit humor aqueous flow under the implant. The support arc sections make contact with the iris and provide the necessary support for the passage arc sections. Auricles extend from the support arc sections and are configured to hold the implant in place by engaging the eye at the iridocorneal angle. The implant may include an artificial lens and preferably spurs on the support arc sections to anchor for the artificial lens.

9 Claims, 5 Drawing Sheets

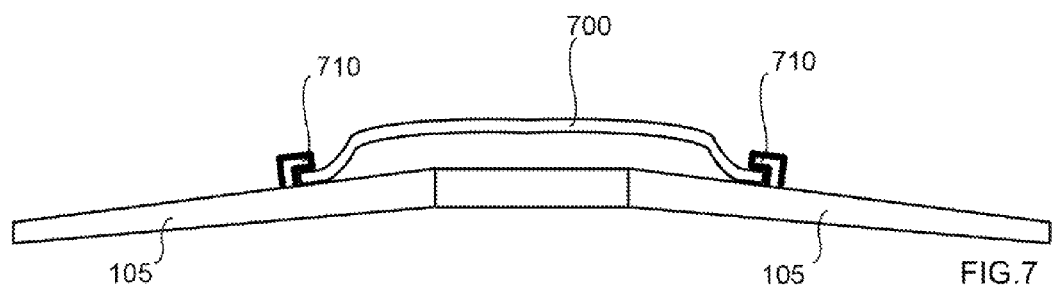
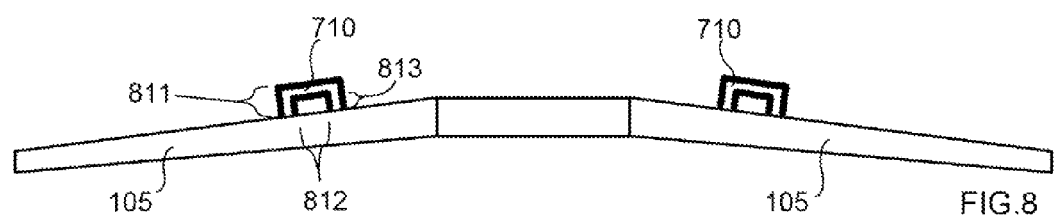
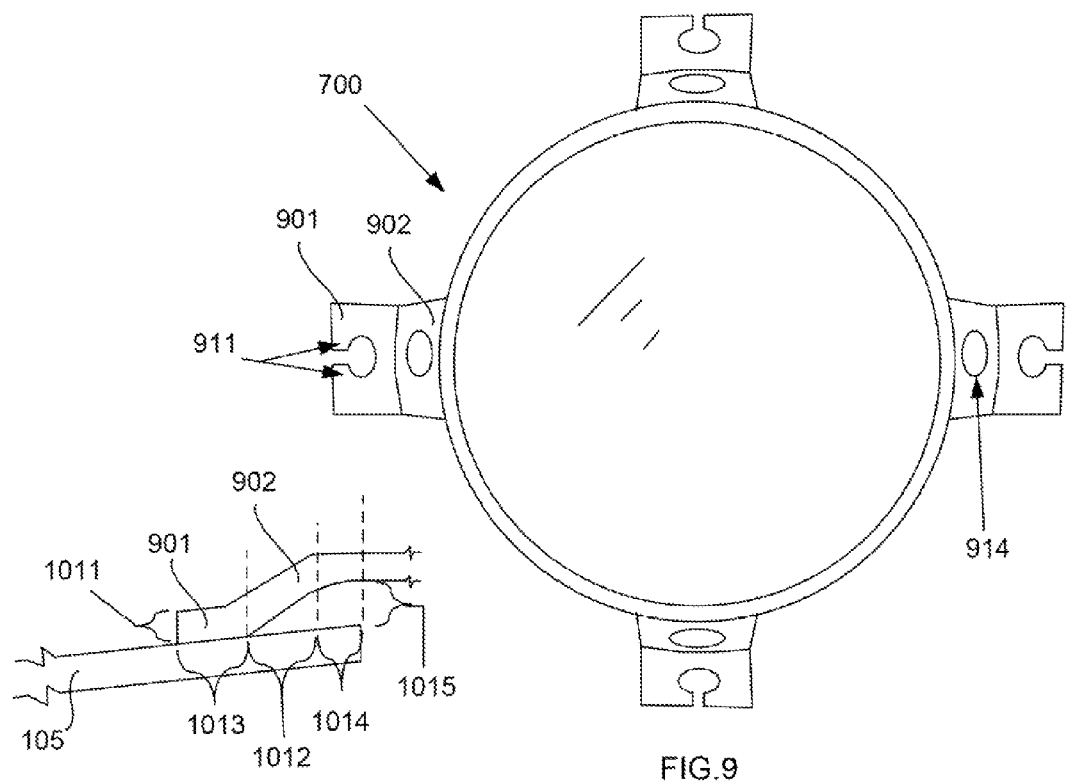

OCULAR IMPLANT IRIS DIAPHRAGM

TECHNICAL FIELD

In the field of eye prosthesis, an ocular implant is in the form of an iris diaphragm adapted to permanently cover the pigmented tissue in front of the crystalline lens of the natural living organ capable of vision or light sensitivity.

BACKGROUND ART

There are numerous medical conditions where changing the color of the eyes is a suitable treatment. These include fixing heterochromia, protecting the eyes of the albinos from the harmful effects of the sunlight, covering up the defects of the iris such as coloboma, severe iris atrophies, and iridoschisis. There is also a need for eye color changes for cosmetic purposes.

An opening in the front of a human eye is called a pupil and it permits entry of light into the eyeball, through the lens of the eye and onto the retina. The size of the pupil is controlled by an iris. The iris has a natural color which is considered the color of the eye.

The state of existing technology in eye implantation of iris overlays in the anterior chamber is disclosed in U.S. Pat. No. 7,025,781 ('781 patent) for an artificial soft iris diaphragm implant. The '781 patent diaphragm is a smooth, flexible and foldable material forming a main portion. In contrast, there is no corresponding main portion in the present implant because it is structured with arc sections that are non-planar, arranged in a non-smooth pattern that enables specific and essential improvements to the performance of the implant.

The '781 patent teaches implants that contain "flap portions" that are "integrally formed with the main portion to provide the diaphragm with a unitary construction." The "main portion" in the '781 patent is "smooth." In contrast, there is no main portion in the present invention because the implant comprises multiple non-uniform and non-planar components in the thicker support arc sections and thinner passage arc sections. These sections differ significantly in thickness and purpose, and define a structure that is non-planar, non-smooth, and non-uniform.

A functional significance of the arc sections of the present invention is that they significantly diminish the contact surface between the implant and the iris, thereby diminishing the postoperative inflammation related to friction between the implant and the iris, reducing the possibility of glaucoma and also preventing the desquamation of the pigment cells into the anterior chamber.

Unlike the '781 patent, only the much thicker support arc sections of the present invention have auricles that extend from the support arc sections of the diaphragm. These auricles that extend from the support arc sections are not an integral part of the passage arc sections of the diaphragm. Unlike the '781 patent, the present invention provides no uniformity between the support arc sections and the passage arc sections.

SUMMARY OF INVENTION

An implant is disclosed for an eye to alter iris color for medical and cosmetic purposes. The implant is made of a material that is inert, nontoxic, foldable and preferably permeable to fluid flow. The material configured to define an annular non-planar structure that fits over the iris yet leaves the natural lens uncovered. The implant extends approximately to the iridocorneal angle. The annular non-planar structure an assembly of two different kinds of arc sections of a non-uniform thickness. These kinds are passage arc sections and support arc sections. The passage arc sections define passages for humor aqueous flow under the implant because they are supported in a position at a distance above the iris. The support arc sections make contact with the iris and provide the necessary support for the passage arc sections. Auricles extend from the support arc sections and are configured to hold the implant in place by engaging the eye at the iridocorneal angle.

The implant may include an artificial lens and with that embodiment, preferably four spurs rise from support arc section and provide an anchor for the artificial lens. The spur may be in any form but two examples include an open angle shape and a closed loop shape. The artificial lens preferably has four haptics or attachment structures to hold the artificial lens in position and to elevate the artificial lens off the top surface of the arc sections. The haptics may be a closed hole to fit over the spur or a sliced hole or pincer to snap in place around a closed-loop-shape spur.

Technical Problem

Existing implants can create significant medical problems due at least in part to interference with humor aqueous flow and excessive contact between the implant and the eye cells. Post implant problems such as ocular hypertension, iritis, corneal oedema, cataracts, glaucoma and infection can lead to the loss of the eye. Problems reported include hyphaema, uncontrolled intraocular pressure, severe endothelial cell loss, bullous keratopathy and anterior uveitis, permanent damage to the trabecular meshwork and corneal endothelium can persist.

Some existing iris prosthesis implants may only be implanted into the posterior chamber, not the anterior chamber in front of the iris or iris remnant because of the danger of damage to the corneal endothelium as well as the danger of severe intraocular pressure increase.

Existing techniques for implantation of aniridia lenses require that the crystalline lens of the patient be removed even if the patient doesn't have a cataract. In other words, the patient has to undergo cataract surgery.

Solution to Problem

An ocular implant within the anterior chamber that covers the iris with a minimal mass, yet permits humor aqueous flow and that has minimal contact with the surface of the iris.

Advantageous Effects of Invention

The ocular implant is useful in treating heterochromia, protecting the eyes of an albino from the harmful effects of the sunlight, covering defects of the iris such as coloboma, severe iris atrophies, and iridoschisis, and for simple cosmetic purposes.

The unique arc sections of ocular implant define passages above the iris which can cut the contact surface with the iris in half while enabling fluid flow of the humor aqueous. The configuration of these arc sections diminishes postoperative inflammation related to friction between the implant and the iris. By diminishing the frictional surface, the implant minimizes the desquamation of the pigment cells into the anterior chamber, which can later cause obstruction in the trabecular meshwork and increased intraocular pressure and resulting glaucoma. These arc sections also avoid the problems inherent in the prior art of obstructing drainage of the humor aqueous from the eye through the trabecular meshwork via the anterior chamber. Thus, the invention decreases the probability of secondary glaucoma.

A primary embodiment of the ocular implant is for treatment when corrective artificial lenses are not needed or desired. This embodiment is non-refractive and is, thus, a solution to medical treatments requiring an unobstructed visual axis using the eye's natural lens. The most prominent advantage of invention over the prior art involving aniridia lenses, is that human crystalline lens is not removed. So, the invention enables subsequent removal of the refractive part for whatever reason.

The ocular implant is supported in the anterior chamber, and is structured to enable humor aqueous flow under the ocular implant.

The ocular implant is much thinner than other implants, which effectively means that reducing the mass of the implant also reduces the potential for adverse effects from adding artificial components to the eye. The ocular implant is held in place at the iridocorneal angle without causing great pressure to the angle structures.

While the ocular implant is designed to be a permanent medical treatment, it can be removed if desired.

The ocular implant may include a lens and the advantages of phakic intraocular lens include no thinning of the cornea and the ability to remove the implanted lens if problems arise or a change in the power of the lens is required. And because the eye's natural lens is left intact, there is no loss in a patient's ability to change focus (if they are under age 40 and do not have presbyopia). This new refractive combination is especially better than existing treatments for astigmatism and is easier to put into the eye. The additional holes for flow of aqueous humor solve the problems of complications due to flow blockage.

BRIEF DESCRIPTION OF DRAWINGS

The drawings illustrate preferred embodiments of the ocular implant according to the invention and the reference numbers in the drawings are used consistently throughout. New reference numbers in FIG. 2 are given the 200 series numbers. Similarly, new reference numbers in each succeeding drawing are given a corresponding series number beginning with the figure number.

FIG. 7 is a side elevation view of the ocular implant with an artificial lens.

FIG. 8 is a sectional side-elevation view of the ocular implant showing a closed-loop-shape spur used to anchor an optional artificial lens to the ocular implant.

FIG. 9 is a plan view of a second lens with a haptic including a pincer used to anchor an optional artificial lens to the ocular implant.

FIG. 10 is a side elevation view of a portion of the second lens atop a portion of the ocular implant.

DESCRIPTION OF EMBODIMENTS

In the following description, reference is made to the accompanying drawings, which form a part hereof and which illustrate several embodiments of the present invention. The drawings and the preferred embodiments of the invention are presented with the understanding that the present invention is susceptible of embodiments in many different forms and, therefore, other embodiments may be utilized and structural, and operational changes may be made, without departing from the scope of the present invention.

Figure 2:
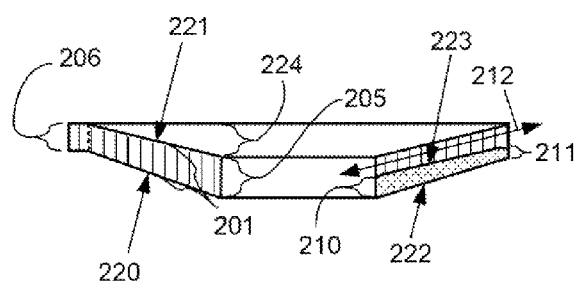
FIG. 2 is an elevation view of the ocular implant at section 2-2 in FIG. 1.
Figure 1:
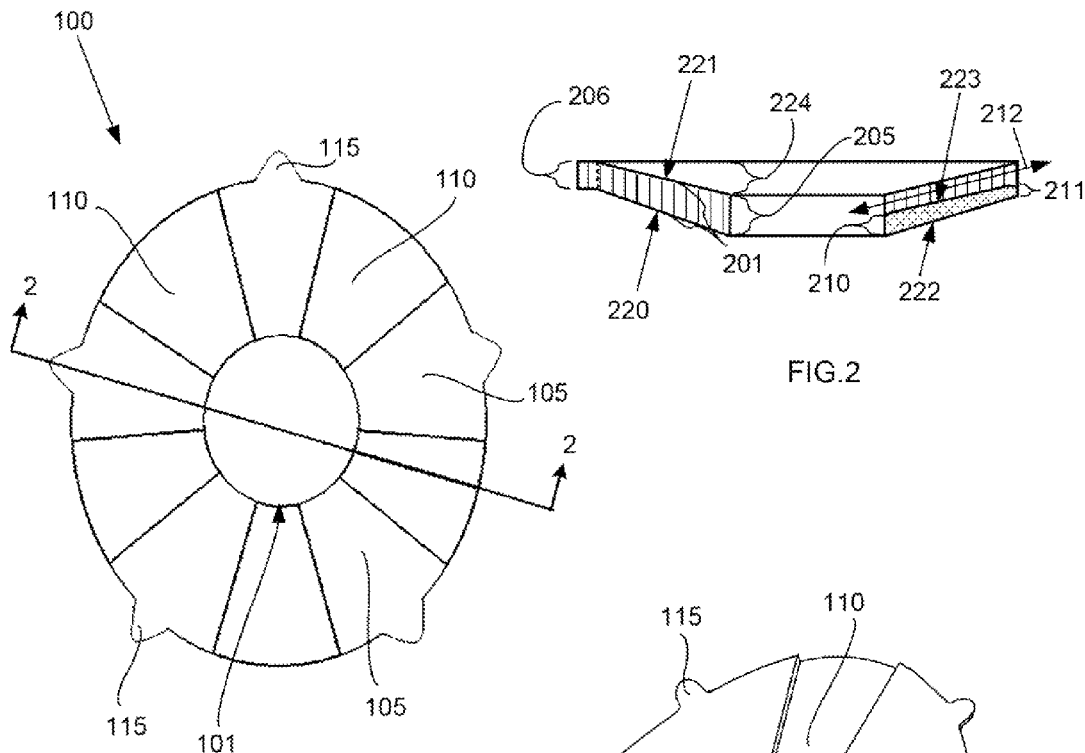
FIG. 1 is a plan view of the ocular implant surface that will face the iris when implanted in the eye.
Figure 3:
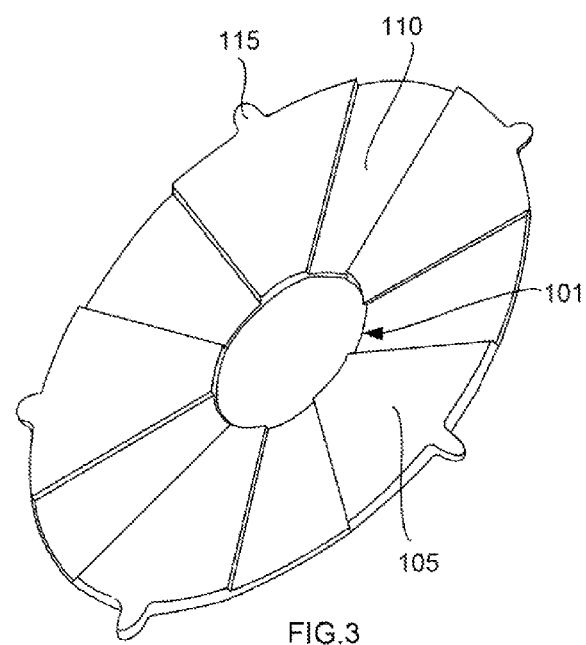
FIG. 3 is a perspective of the ocular implant surface shown in FIG. 1.
Figure 4:
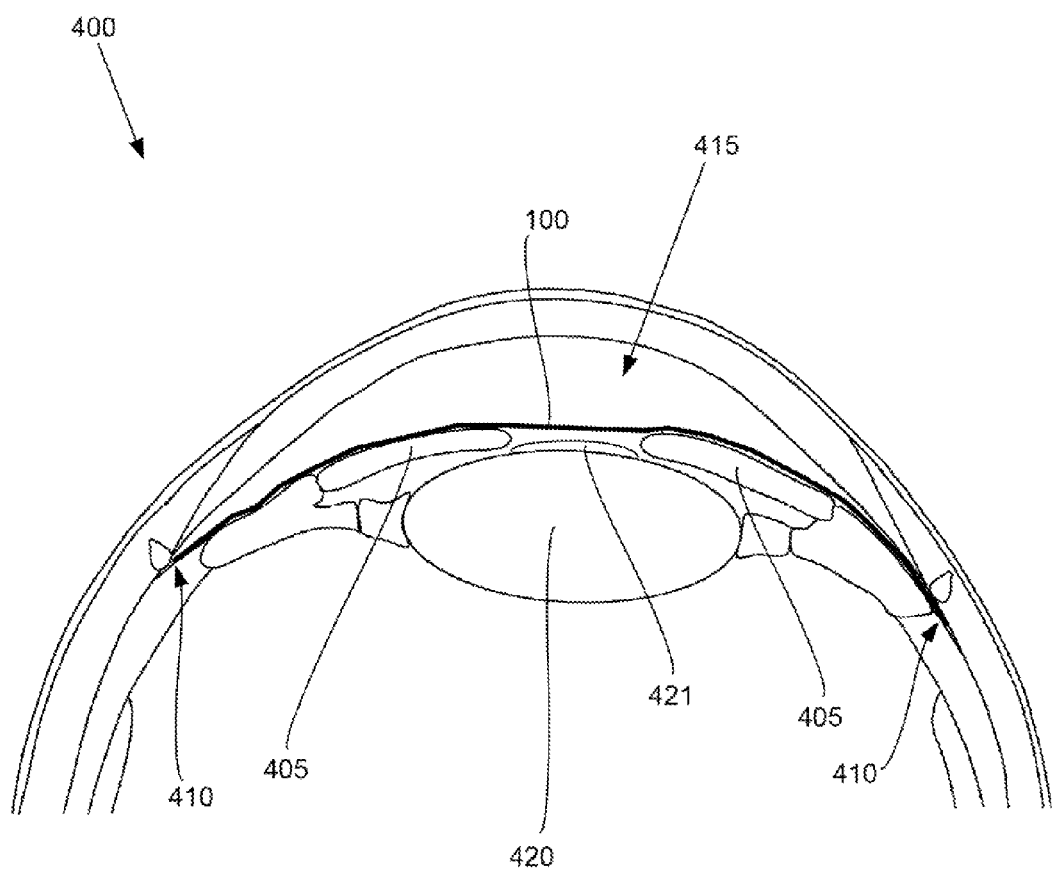
FIG. 4 is an elevation of a vertically-oriented eye showing the location of the ocular implant within the eye.

FIGS. 1-3 show a preferred embodiment of the ocular implant in several views and FIG. 4 shows after implantation within an eye. The preferred embodiment is an implant (100) for an eye (400), the eye (400) comprising an anterior chamber (415), an iridocorneal angle (410), a natural lens (420), and an iris (405), the implant (100) configured to extend over the iris (405) within the anterior chamber (415) to alter iris (405) color for medical and cosmetic purposes. Both sides of the implant can be colored, but preferably only the top surface, that is the surface not in contact with the iris (405), is colored.

The implant (100) includes a material that is inert, nontoxic and foldable, which is configured to define an annular non-planar structure. This material is preferably a hydrophilic acrylic, silicone or plastic with elasticity, flexibility and biocompatible. Heparin surface modification of intraocular implants has been shown to diminish postoperative inflammation to enhance biocompatibility. Accordingly, heparin surface modification may be performed in order to augment the biocompatibility of the implant.

Figure 13:
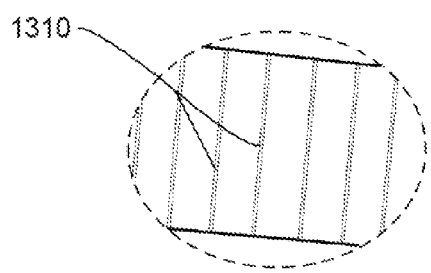
FIG. 13 is a magnification showing micro-holes through the ocular implant.

The material is optionally configured to define a plurality of microscopic holes to render the material permeable to fluid within the eye (400). FIG. 13 is a magnification of the portion (13) of the ocular implant shown in FIG. 11 to illustrate the microscopic holes (1310) that permit aqueous humor flow through the ocular implant. These microscopic holes (1310) are throughout the ocular implant in both support arc sections (105) and passage arc sections (110).

The annular non-planar structure is configured to leave the natural lens (420) uncovered and is further configured to extend approximately to the iridocorneal angle (410) (also known as the iridial angle) when implanted in the eye (400) atop the iris (405). The annular non-planar structure, thus, includes, in preferred embodiments, a central opening corresponding to the pupil (421) of the human eye. For human eyes, the central opening is usually between 3 to 4 millimeters in diameter, preferably about 3.5 millimeters in diameter.

The annular non-planar structure includes a plurality of arc sections (105 and 110) of a non-uniform thickness (201) diminishing from the central opening to the periphery, that is, in a radial direction away from the central opening. The arc sections include support arc sections (105) and passage arc sections (110).

Each arc section comprises a top surface and a bottom surface. Thus, there is a support-arc-section top-surface (220); a support-arc-section bottom-surface (221); a passage-arc-section top-surface (222); and a passage-arc-section bottom-surface (223). The top surface designation is generally that which is away from the iris (405) when implanted in the eye (400). When implanted, the distance or vault height (224)

from the surface of the iris (405) at the edge of the central opening to the support-arc-section bottom-surface (221) is typically about 0.3 to 0.5 millimeters. With this vault height (223), it has an anatomic compatibility with the iris (405) in the anterior chamber (415) of the eye (400).

The arc sections are configured, when implanted in the eye (400) atop the iris (405), to define passages (212), indicated by the double arrow, for humor aqueous flow under the implant (100) formed by passage arc sections (110) that sit a distance above the iris (405). The passage arc sections (110) uniquely enable flow of the humour aqueous between the pupil and the trabecular meshwork at the iridocorneal angle.

The arc sections are configured, when implanted in the eye (400) atop the iris (405), to define a support structure for the passages (212) formed by support arc sections (105) that are in contact with the iris (405). Such contact with the iris (405) is typically limited to the area near the periphery of the support arc sections (105) at the iridocorneal angle (410). When implanted, the support-arc-section bottom-surface (221) and the passage-arc-section bottom-surface face the iris (405).

Each of the support arc sections (105) is a thick part tapering outwardly, that is, towards the periphery. The support-arc-section maximal thickness (205) is preferably about 0.16 to 0.18 millimeters thick near the central opening. The support-arc-section minimal thickness (206) is preferably about 0.12 to 0.14 millimeters thick at the periphery.

Each of the passage arc sections (110) is similarly configured but with different preferably tapered thicknesses. The passage-arc-section maximum thickness (210) is preferably about 0.08 to 0.12 millimeters thick near the central opening. The passage-arc-section minimum thickness (211) is preferably about 0.06 to 0.1 millimeters at the periphery. Preferably the minimum space between the bottom of the passage arc sections (110) and the iris at the iridocorneal angle (410) is about 0.04 millimeters.

The annular non-planar structure includes a plurality of auricles (115) extending from the support arc sections (105) and configured to hold the implant (100) in place by engaging the eye (400) at the iridocorneal angle (410). The auricles (115) preferably have a triangular shape when viewed from the top and are to hold or stabilize the implant (100) in a fixed position within the eye (400). Semi-circular or rounded rectangular shapes are alternatives. Each of the auricles (115) is preferably 0.12 to 0.14 millimeters thick and is preferably configured with microscopic holes to make it permeable to fluid flow within the eye (400). The auricles are preferably the same thickness as the support arc sections (105). The base length of the triangle is preferably 0.8 to 1.0 millimeters and its height or distance extended from a circle defining most of the support arc sections (105) is preferably 0.3 to 0.5 millimeters. The auricles (115) are preferably evenly spaced from each other and the passage arc sections (110). The auricles (115) are preferably configured with a rounded end to help minimize damage to structures of the iridocorneal angle (410). The rounded end is one that is not sharp and having an obtuse angle with the support arc section.

When properly configured, the auricles (115) cause almost no stress to angle structures, yet keep the implant in place integrally with its thin, elastic and soft nature. The auricles (115) safely distribute any pressure forces from the ocular tissues over multiple contact points. The auricles (115) should be maximally flexible to keep the implant (100) in the desirable location (immediately above the iris) avoiding any compression that could potentially result above or below the implant. The overall diameter of the implant to the ends of the auricles (115) is preferably between 11.5 to 13.5 millimeters.

Thus, the diameter of the circle defining most of the support arc sections (105) is preferably between 10.5 to 12.5 millimeters.

As shown in FIG. 2, each passage arc section (110) is uniformly thinner than each support arc section (105). Also the bottom of the passage arc section (110) is above the bottom of the support arc section (105) in order to form the passage (212).

Figure 5:
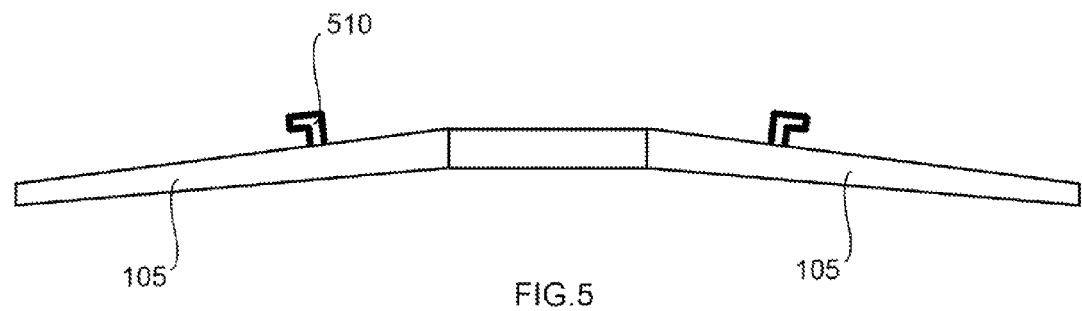
FIG. 5 is a sectional side-elevation view of the ocular implant showing an open-angle-shape spur used to anchor an optional artificial lens to the ocular implant.

FIGS. 5, 7 and 8 illustrate the implant (100) with two versions of an optional spur: FIG. 5 illustrates an outwardly-facing-open-angle-shape spur (510) and FIG. 7 and FIG. 8 illustrate a closed-loop-shape spur (710), which are used to secure an artificial lens that is also an optional addition to the ocular implant. The optional first artificial lens (600) is used with the outwardly-facing-open-angle-shape spur (510) and the optional second artificial lens (700) is used with the closed-loop-shape spur (710). The term "outwardly" refers generally to a direction away from the natural lens (420).

In any of the spur versions, the spur rises from a support arc section (105) away from the iris (405) when implanted in the eye (400) and is configured to provide an anchor point for an artificial lens spanning the natural lens (420) atop the implant (100).

The closed-loop-shape-spur height (811) is preferably in a range of 0.2 to 0.6 millimeters. The closed-loop-shape-spur-opening width (812) is preferably about 0.1 millimeters. The closed-loop-shape-spur-opening height (813) is preferably in a range of about 0.1 to 0.3 millimeters.

FIG. 7 illustrates the implant (100) with the optional second artificial lens (700). This embodiment includes an optional second artificial lens (700), which has as a distinguishing feature a pincer (911) on the second lens haptic foot (901). The first-lens-haptic-foot width (612) is preferably in a range of about 0.35 to 0.75 millimeters and the first-lens-haptic-foot length (613) is preferably in a range of about 0.15 to 0.5 millimeters.

The optional first artificial lens (600) and the optional second artificial lens (700) are refractive components, that is, each is a phakic intraocular lens, typically used to correct high refractive errors, which are not eligible for LASIK (laser-assisted in situ keratomileusis) surgery. An implantable lens is often needed when other vision correction procedures are not a good medical choice, such as when a person has thin corneas or myopia between 3.00 and 20.00 diopters. With some patients receiving phakic intraocular lens, LASIK may be used as a follow-up to refine vision correction.

In any of the embodiments using an artificial lens, the haptic is configured to engage the spur to hold the artificial lens in position and to elevate the artificial lens off the top surface of the implant and the iris. This is illustrated in FIG. 10, which is a side elevation view of a portion of the optional second artificial lens (700) atop a portion of the support arc section (105). The second-lens-haptic thickness (1011) is preferably in a range of 0.1 to 0.3 millimeters. The second-lens-haptic-foot length (1013) is preferably in a range of 0.15 to 0.5 millimeters. The second-lens-haptic-rise distance (1012) is preferably in a range of 0.25 to 0.5 millimeters. The second-lens-haptic-frame distance (1014) is preferably about 0.5 millimeters. The second-lens-haptic height (1015) is preferably in a range of 0.25 to 0.5 millimeters.

Figure 6:
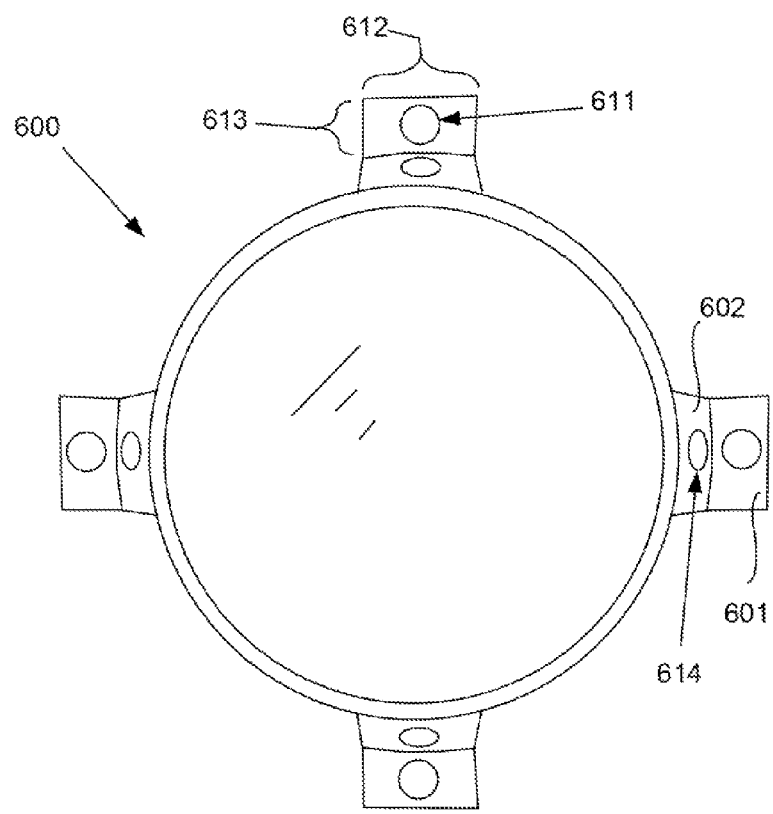
FIG. 6 is a first-lens haptic with closed-hole to secure to the spur shown in FIG. 5.

Preferably, there are four haptics, evenly spaced from each other, as shown in FIGS. 6 and 9. The diameter of the refractive part is greater than the diameter of the central opening of the non-refractive part. Both the non-refractive part and any optional artificial lens are also foldable, biocompatible materials. It is noted that the number and thickness of the arc sections may vary to suit the application, for example with or without an artificial lens.

In the example lenses shown in FIGS. 6 and 9, the haptic comprises a riser to elevate the artificial lens: namely the first-lens haptic riser (602) elevates the optional first artificial lens (600); and a second-lens haptic riser (902) elevates the optional second artificial lens (700). The riser is configured to define a hole to enable free flow of humour aqueous under the artificial lens. For the optional first artificial lens (600), this hole (614) is shown in the first-lens haptic riser (602). For the optional second artificial lens (700), this hole (914) is shown in the second-lens haptic riser (902).

Since the implant (100) is flexible, it is readily folded and inserted into the eye through a peripheric corneal surgical incision about 3.5 millimeters long. The cornea need not be sutured for this incision length. This is a very simple, short, safe and painless procedure. When an optional first artificial lens (600) is used, after placing the non-refractive part properly in the anterior chamber (415), the refractive part is inserted through the same incision, since it is also foldable. Then, each of the four haptics in a preferred embodiment is then engaged on the spur rising from the support-arc-section top-surface (220).

Figure 11:
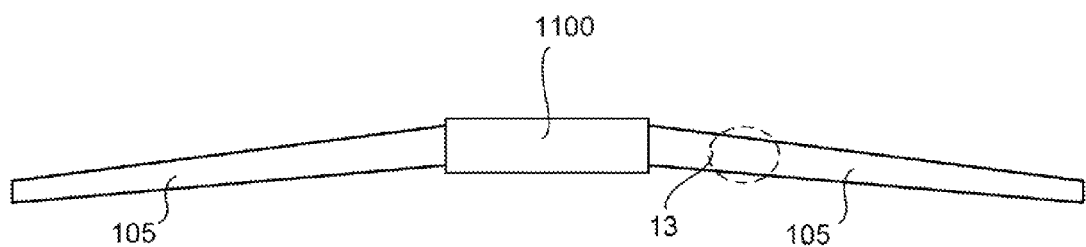
FIG. 11 is a sectional side elevation view of an ocular implant with a third artificial lens.
Figure 12:
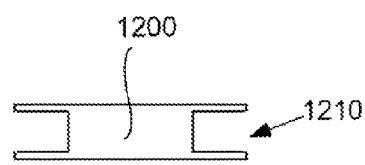
FIG. 12 is a side elevation view of a fourth artificial lens.

The additional refractive part, also referred to as the artificial lens, is preferably placed at the level of the center of the main non-refractive body, also referred to as the implant (100). So the combination of artificial lens and implant (100) will allow the surgeon to insert the unit easily. The surgeon will not have to deal with attaching the refractive part, namely the artificial lens, after he/she inserts the main non-refractive, color part, namely the implant (100). When main body, namely the implant (100) is placed properly, the refractive part will be placed at the same time. These versions are illustrated in FIG. 11 and FIG. 12. Of course, the refractive part (artificial lens) is preferably clear in all versions and not colored. The microscopic holes (1310), or pores, on the passage arc sections in combination with the flow under the passage arc sections, will more enable maximal natural aqueous humor flow.

FIG. 11 is a sectional side elevation view of an ocular implant with a third artificial lens (1100). This is a monoblock combination ocular implant and artificial lens that does not employ spurs to affix the artificial lens. The refractive part, that is namely the third artificial lens (1100), is at the level of the central opening, not above or below it.

FIG. 12 is a side elevation view of a fourth artificial lens (1200) configured with a slot (1210) to receive the ocular implant. This embodiment with a non-refractive part and a refractive lens does not include spurs.

For any of the embodiments employing an artificial lens the ocular implant is configured to cover the natural lens when the implant is implanted in the eye atop the iris.

The above-described embodiments including the drawings are examples of the invention and merely provide illustrations of the invention. Other embodiments will be obvious to those skilled in the art. Thus, the scope of the invention is determined by the appended claims and their legal equivalents rather than by the examples given.

INDUSTRIAL APPLICABILITY

The invention has application to the medical industry.

What is claimed is:

1. An implant for an eye, the eye comprising an anterior chamber, an iridocorneal angle, a natural lens, and an iris, the implant configured to extend over the iris within the anterior chamber to alter iris color for medical and cosmetic, purposes, the implant comprising:
    a material that is inert, nontoxic and foldable, the material configured to define an annular non-planar structure with a central opening and a periphery,
    the annular non-planar structure configured to leave the natural lens uncovered and further configured to extend approximately to the iridocorneal angle when implanted in the eye atop the iris;
    the annular non-planar structure comprising a plurality of arc sections, the arc sections comprising support arc sections of a non-uniform thickness that diminishes from the central opening to the periphery and passage arc sections, wherein each arc section comprises a top surface and a bottom surface,
    the arc sections configured, when implanted in the eye atop the iris, to define:
    passages for humor aqueous flow under the implant formed by passage arc sections that sit a distance above the iris; and,
    a support structure for the passages formed by support arc sections that are in contact with the iris; and,
    auricles extending from the support arc sections and configured to hold the implant in place by engaging the eye at the iridocorneal angle.
2. The implant of claim 1, wherein the material is configured to define a plurality of microscopic holes to render the material permeable to fluid within the eye.
3. The implant of claim 1, further comprising a spur rising from a support arc section away from the iris when implanted in the eye and configured to provide an anchor point for an artificial lens spanning the natural lens atop the implant.
4. The implant of claim 3, wherein the spur comprises an open angle shape.
5. The implant of claim 3, wherein the spur comprises a closed loop shape.
6. The implant of claim 3, further comprising an artificial lens comprising a haptic configured to engage the spur to hold the artificial lens in position and to elevate the artificial lens off the top surface of the arc sections.
7. The implant of claim 6, wherein the haptic is configured with a closed hole.
8. The implant of claim 6, wherein the haptic is configured with a pincer.
9. The implant of claim 1, further comprising an artificial lens configured to cover the natural lens when the implant is in the eye atop the iris.

* * * * *